US005622849A

United States Patent [19]

Fusho et al.

[11] Patent Number: 5,622,849

[45] Date of Patent: Apr. 22, 1997

[54] CATALASE FROM BACILLUS AND PROCESS FOR PRODUCING THE SAME

[75] Inventors: Yuichi Fusho, Kanagawa; Yoshihiro Yajima, Chiba, both of Japan

[73] Assignee: Showa Denko K.K., Tokyo, Japan

[21] Appl. No.: 517,545

[22] Filed: Aug. 21, 1995

Related U.S. Application Data

[63] Continuation of Ser. No. 354,721, Dec. 6, 1994, Pat. No. 5,486,467.

[30] Foreign Application Priority Data

| | | | |
|---|---|---|---|
| Jan. 18, 1994 | [JP] | Japan | 6-3698 |
| Apr. 25, 1994 | [JP] | Japan | 6-86745 |

[51] Int. Cl.$^6$ .......... C12N 9/08

[52] U.S. Cl. .......... 435/192; 435/183; 435/252.1

[58] Field of Search .......... 435/192, 183, 435/252.1

[56] References Cited

U.S. PATENT DOCUMENTS

| | | | |
|---|---|---|---|
| 3,123,539 | 3/1964 | Beers, Jr. | 435/192 |
| 4,460,686 | 7/1984 | Hartmeier | 435/192 |
| 5,155,041 | 10/1992 | Bok et al. | 435/252.1 |

FOREIGN PATENT DOCUMENTS

| | | |
|---|---|---|
| 220332 | 12/1983 | Germany . |
| 55-135588 | 10/1980 | Japan . |
| 63-3788 | 1/1988 | Japan . |
| 1168281 | 7/1989 | Japan . |
| 276579 | 3/1990 | Japan . |
| 420288 | 1/1992 | Japan . |
| 5153975 | 6/1993 | Japan . |
| WO9217571 | 10/1992 | WIPO . |

OTHER PUBLICATIONS

Ishida et al, *Kumamoto J. Sci. Biol.*, 15(2):39–48 (1981).
Lowen et al, *J. of Bacteriology*, 169(8):3601–3607 (1987).
Lowen et al, *J. of Bacteriology*, 169(12):5848–5851 (1987).
Lowen et al, *Biochem. Cell Biol.*, 64:638–646 (1986).
Lowen et al, *Biochem. Cell Biol.*, 65:939–947 (1987).
Lowen et al, *Biochem. Cell Biol.*, 66:707–714 (1988).

*Primary Examiner*—Michael G. Wityshyn
*Assistant Examiner*—Blaine Lankford
*Attorney, Agent, or Firm*—Sughrue, Mion, Zinn, Macpeak & Seas

[57] ABSTRACT

A microbial catalase having a catalase activity at 0° C. of 95% or more of its catalase activity at 30° C., when measured at pH 7, and a process for producing the same. The microbial catalase preferably has (1) an operative temperature of 0° to 60° C. and an optimum temperature of 0° to 30° C., when measured within the range of from 0° to 60° C., (2) an optimum pH of 7 to 10, (3) a resistance to 10 mM potassium fluoride, (4) a molecular weight is 65,000±3,000, when measured by SDS polyacrylamide gel electrophoresis, and (5) an isoelectric point is about 4.8, when measured by isoelectric focusing.

4 Claims, 3 Drawing Sheets

(OPTIMUM TEMPERATURE)

(OPTIMUM pH)

(pH STABILITY)

CATALASE FROM BACILLUS AND PROCESS FOR PRODUCING THE SAME

This is a Continuation of Parent application Ser. No. 08/354,721, filed Dec. 6, 1994, now U.S. Pat. No. 5,486,467.

FIELD OF THE INVENTION

The present invention relates to a catalase which shows high catalase activity at low temperature and a process for the production thereof. Since the catalase of the present invention has a function to hydrolyze hydrogen peroxide even at a low temperature, it can be applied advantageously, for example, to the wastewater treatment during the winter season and the treatment of wastewater after bleaching perishables such as herring roe, in addition to its use at ordinary or more higher temperatures.

BACKGROUND OF THE INVENTION

Catalase has been used widely, for example, in the semiconductor process for the treatment of hydrogen peroxide-containing waste water, in the fiber bleaching process for the hydrolysis of remaining hydrogen peroxide, and in the field of food industry for the hydrolysis of hydrogen peroxide remained after bleaching perishables such as herring roe and the like.

Catalase is an enzyme which hydrolyzes hydrogen peroxide and is known to be produced by a great variety of organisms. Examples of catalase of microbial origin so far reported include a thermostable catalase produced by a bacterium belonging to the genus Thermus (as described in JP-A-55-135588), a fluoride ion-resistant catalase produced by a bacterium belonging to the genus Micrococcus (as described in JP-A-4-20288), a halotolerant catalase produced by a yeast belonging to the genus Hansennula (as described in JP-A-63-3788), and a thermostable catalase produced by a fungus belonging to the genus Aspergillus (as described in JP-A-5-153975). (The term "JP-A" used herein means an unexamined published Japanese patent application.)

However, conventionally used catalases are not satisfactory in terms of their catalase activity under low temperature conditions.

SUMMARY OF THE INVENTION

An object of the present invention is to provide a catalase capable of showing excellent catalase activity at low temperatures in comparison with the prior art catalases.

Other objects and effects of the present invention will be apparent from the following description.

The inventors of the present invention have conducted intensive studies on a catalase capable of showing high catalase activity at low temperatures through screening of microorganisms from stock cultures and natural sources. As the result, the inventors have found that a catalase produced by *Bacillus subtilis* IAM 1026 can show high catalase activity even at low temperatures, thus resulting in the accomplishment of the present invention.

Accordingly, the present invention relates to:

(1) A microbial catalase having a catalase activity at 0° C. of 95% or more of its catalase activity at 30° C., when measured at pH 7.

(2) A microbial catalase as described in item (1) above, wherein the catalase has:

(a) an operative temperature of 0° to 60° C. and an optimum temperature of 0° to 30° C., when measured within the range of from 0° to 60° C., (b) an optimum pH of 7 to 10, (c) a resistance to 10 mM potassium fluoride, (d) a molecular weight of 65,000±3,000, when measured by SDS polyacrylamide gel electrophoresis, and (e) an isoelectric point of about 4.8, when measured by isoelectric focusing.

(3) A microbial catalase as described in item (1) or (2) above, wherein the catalase is originated from a bacterium.

(4) A microbial catalase as described in item (3) above, wherein the bacterium belongs to the genus Bacillus.

(5) A microbial catalase as described in item (3) above, wherein the bacterium is *Bacillus subtilis.*

(6) A microbial catalase as described in item (3) above, wherein the bacterium is *Bacillus subtilis* IAM 1026 or a mutant strain thereof.

(7) A process for producing a catalase as described in item (1) or (2) above, the process comprising culturing *Bacillus subtilis* IAM 1026 or a mutant strain thereof.

DETAILED DESCRIPTION OF THE INVENTION

Figure 1:
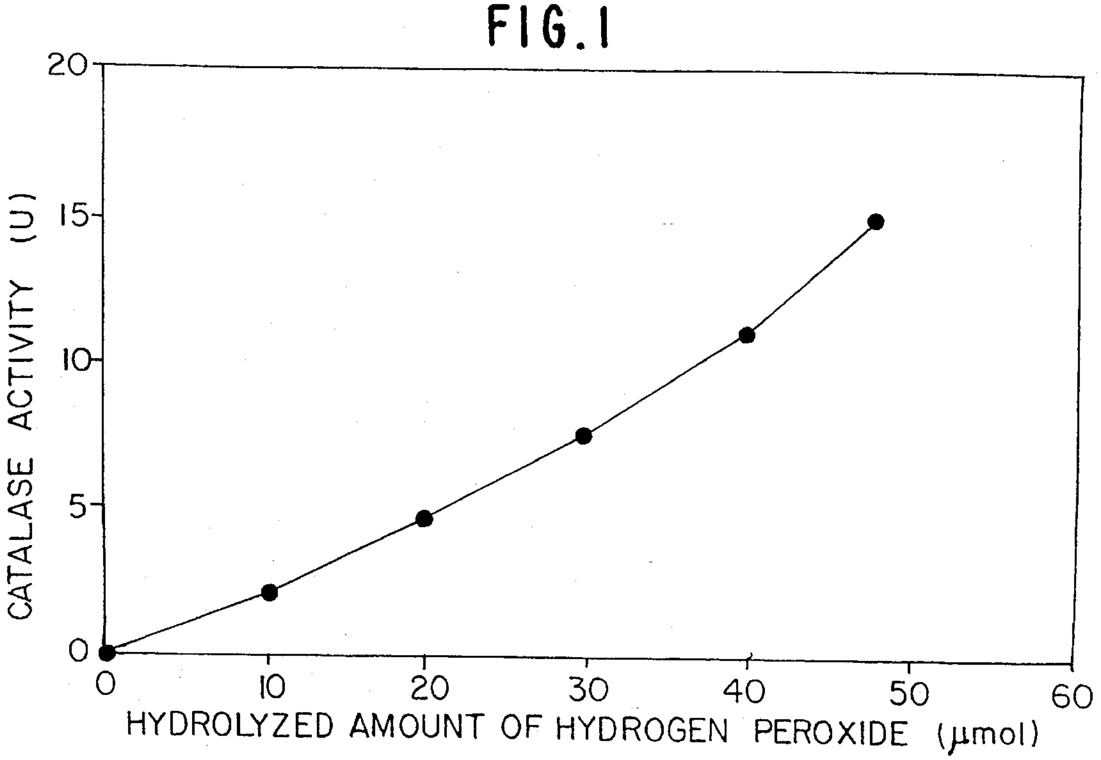
FIG. 1 is a graph showing a standard reaction curve for use in the measurement of catalase activity.

Methods for the measurement of catalase activity used for the screening of catalase are firstly described in the following, while catalase activity measurement of the catalase of the present invention is not limited to these methods.

Activity Measuring Method 1

This method is carried out in accordance with the procedure in which catalase is allowed to act upon hydrogen peroxide used as a substrate, and decrease in the concentration of hydrogen peroxide resulting from the hydrolysis of hydrogen peroxide is measured based on the absorption at 240 nm, as described in H. Aebi et al, *Method Enzyme Analysis*, vol. 2, p. 675 (1974).

Specifically, 3 ml of a 50 mM phosphate buffer (pH 7.0) is put into a blank side cell in a constant temperature cell chamber controlled at 25° C., a 3 ml portion of 50 mM phosphate buffer containing 460 ppm of hydrogen peroxide is put into a sample side cell in the chamber, and the reaction is started by adding 100 μl of an adjusted enzyme solution prepared by appropriately diluting each enzyme solution to be tested. During the reaction, absorbance at a wavelength of 240 nm is recorded to calculate decreasing rate of hydrogen peroxide. Catalase activity in the enzyme solution to be tested is calculated in accordance with the following equation. In this case, 1 U represents an activity to hydrolyze 1 μmol of hydrogen peroxide in 1 minute.

$$\text{Catalase activity (U/ml)} = (\Delta E \div 43.6 \times 1{,}000 \times (3{,}000 + 100)/100) \times n = \Delta E \times 711 \times n$$

In this equation, ΔE represents a decrease in absorbance in 1 minute; 43.6 is the absorption coefficient of 1 mol/l (=1 mmol/ml) hydrogen peroxide solution; 1,000 is the catalase activity (U) to hydrolyze 1 mmol of hydrogen peroxide in 1 minute; (3,000+100)/100 is the dilution factor of each adjusted enzyme solution due to the addition of the adjusted enzyme solution to the substrate solution; and n represents a dilution factor when each enzyme solution to be tested is appropriately diluted to prepare an adjusted enzyme solution.

Activity Measuring Method 2

This method is carried out in accordance with a procedure in which hydrogen peroxide remained after the enzyme reaction is titrated with sodium thiosulfate, as described in *Kouso Riyou Handbook* (Enzyme Application Handbook), edited by M. Ozaki, published by Chijinshokan (Japan), p. 404–410 (1985).

Specifically, 5 ml of a substrate solution prepared by diluting commercially available 30% by weight hydrogen peroxide with a 50 mM phosphate buffer (pH 7.0) by a factor of 800 is put into a container and thermostated by dipping the container in a constant-temperature water bath controlled at 30° C. A 1 ml portion of each enzyme solution to be tested, which is warmed up to 30° C., is added to the substrate solution, and the enzyme reaction is stopped exactly 5 minutes thereafter by rapidly adding 2 ml of 1N sulfuric acid. 1 ml of 10% potassium iodide solution and 1 drop of 1% ammonium molybdate are added thereto, subsequently titrating free iodine with 0.005N sodium thiosulfate using a starch indicator. A 1 ml portion of 0.005N sodium thiosulfate is equivalent to 2.5 μmol of hydrogen peroxide. Separately, a blank test is carried out by repeating the same procedure as above except that the enzyme solution is added after adding 1N sulfuric acid.

The amount of hydrogen peroxide hydrolyzed by the catalase reaction is calculated by subtracting the measured value for the sample from that of the blank test to obtain catalase activity of the enzyme solution to be tested using the standard reaction curve shown in FIG. 1. In this case, 1 U represents an activity to hydrolyze 1 μmol of hydrogen peroxide in 1 minute.

The following shows properties of the catalase of the present invention.

(1) Operative Temperature and Optimum Temperature

Figure 2:
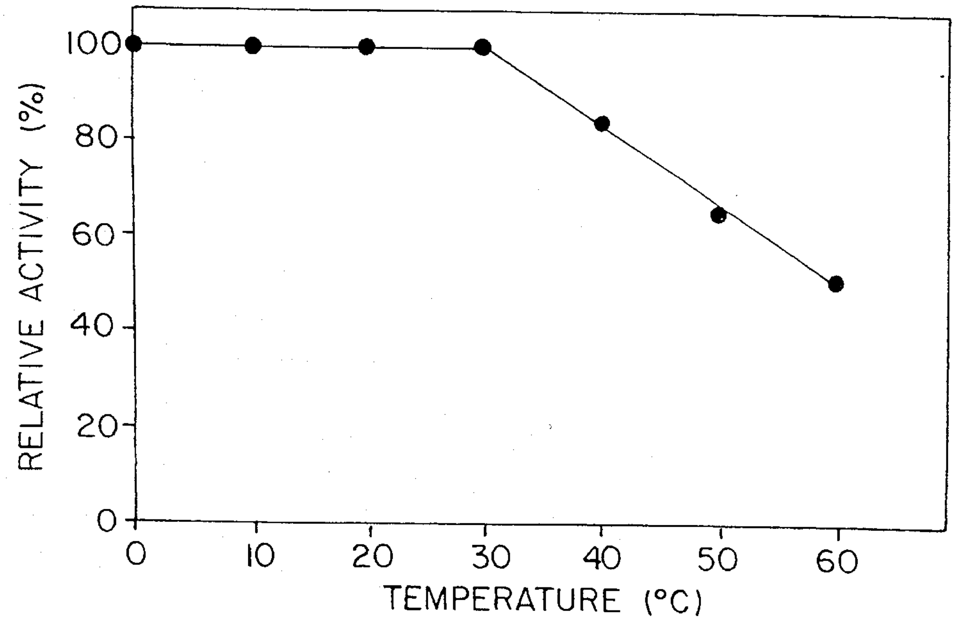
FIG. 2 is a graph showing operative temperature and optimum temperature of the catalase of the present invention.

The catalase activity at various temperatures within the range of from 0° to 60° C. was measured at pH 7.0 in accordance with the aforementioned Activity Measuring Method 2, and the results were compared taking the activity value at 30° C. as 100. As shown in FIG. 2, when measured within the range of from 0° to 60° C., the catalase of the present invention was capable of reacting at a temperature of from 0° to 60° C., with an optimum temperature range being from 0° to 30° C. It showed 95% or more of the catalase activity measured at 30° C. even at a low temperature of from 0° to 10° C.

(2) Thermal Stability

Figure 3:
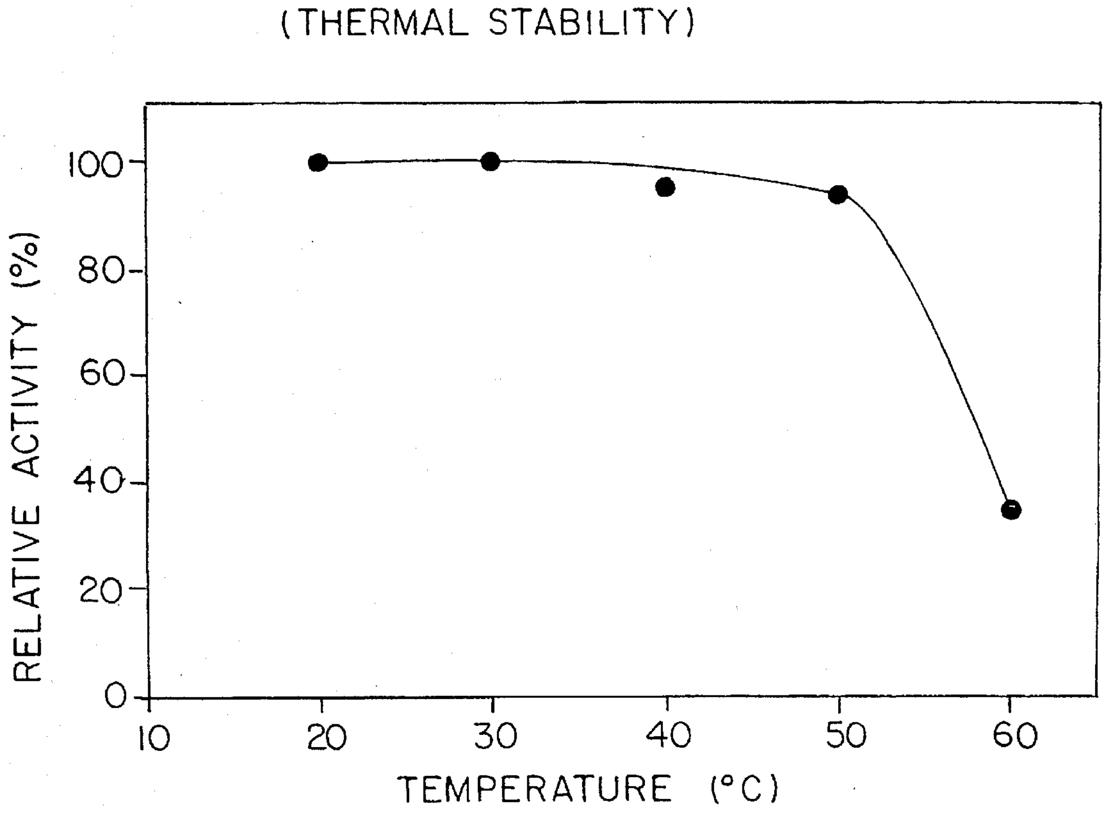
FIG. 3 is a graph showing thermal stability of the catalase of the present invention.

Residual catalase activity after 30 minutes of incubation at pH 7.0 under varied temperature conditions was measured in accordance with the aforementioned Activity Measuring Method 2, and the results were compared taking the activity value at 30° C. as 100.As shown in FIG. 3, the catalase of the present invention was stable up to 50° C., but its residual activity at 60° C. was 34%.

(3) Operative pH and Optimum pH

Figure 4:
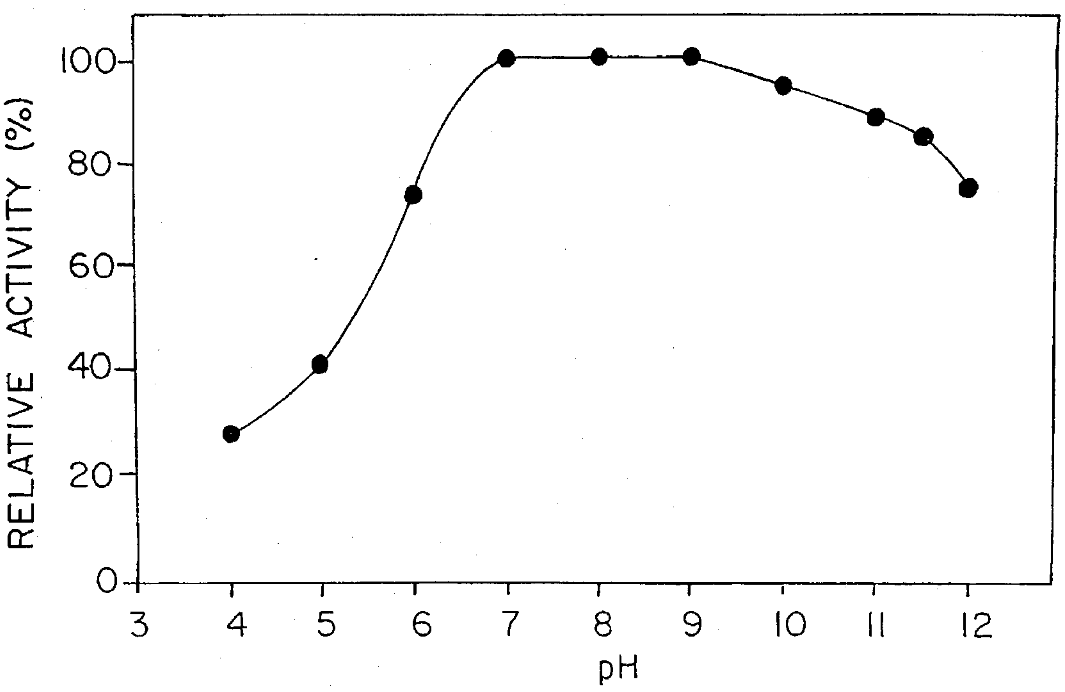
FIG. 4 is a graph showing operative pH and optimum pH of the catalase of the present invention.

The catalase activity at 30° C. was measured at various pH values in accordance with the aforementioned Activity Measuring Method 2, and the results were compared taking the activity value at pH 7.0 as 100. As shown in FIG. 4, when the activity was measured at varied pH values of from 4 to 12, the catalase of the present invention was capable of reacting at a pH value of from 4 to 12, with an optimum pH range being from 7 to 10.

(4) pH Stability

Figure 5:
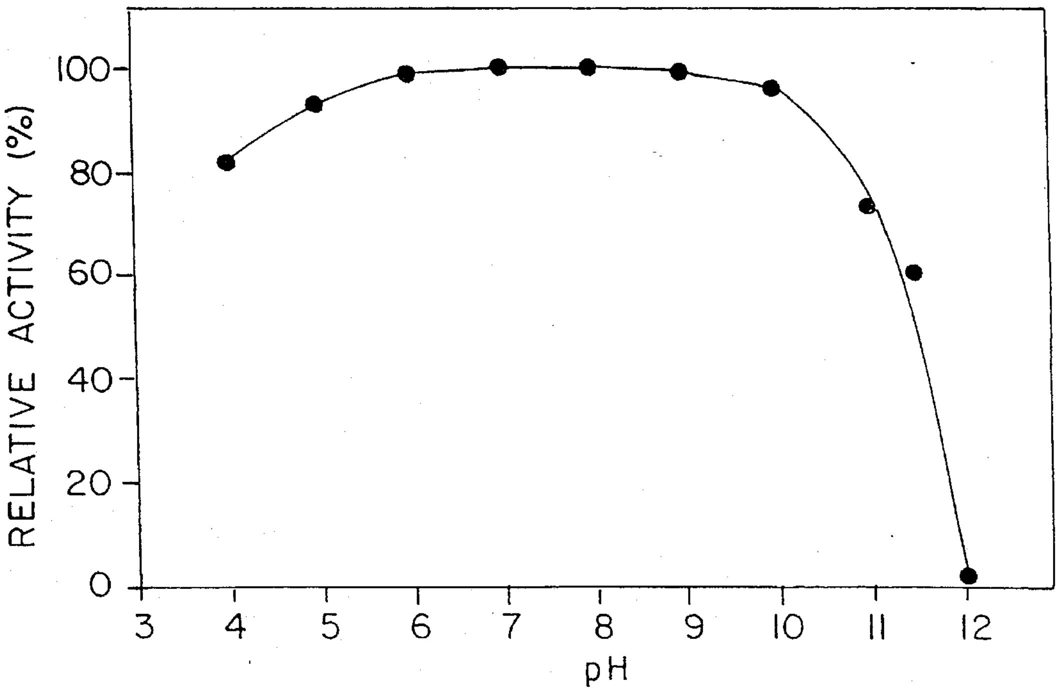
FIG. 5 is a graph showing pH stability of the catalase of the present invention.

Residual catalase activity after 30 minutes of incubation at 30° C. under various pH conditions was measured in accordance with the aforementioned Activity Measuring Method 2, and the results were compared taking the activity value at pH 7.0 as 100. As shown in FIG. 5, the catalase of the present invention was stable at a pH value within the range of from 6 to 10.

(5) Resistance to Fluoride Ions

In accordance with the aforementioned Activity Measuring Method 1, the adjusted enzyme solution was added to a 50 mM phosphate buffer solution containing 10 mM potassium fluoride to measure the activity which was then compared with that of a control measured in the absence of the fluoride, with taking the latter as 100. The catalase of the present invention had resistance to 10 mM potassium fluoride, since it showed 96% of its activity even in the presence of 10 mM potassium fluoride.

(6) Molecular Weight

The molecular weight was measured by SDS-polyacrylamide gel electrophoresis, and the catalase of the present invention was found to have a molecular weight of 65,000±3,000. A pre-stained SDS-polyacrylamide gel electrophoresis standard kit manufactured by Bio-Rad Corp. was used as molecular markers. The kit was composed of rabbit muscle phosphorylase B (molecular weight: 106,000), bovine serum albumin (molecular weight: 80,000), chick egg ovalbumin (molecular weight: 49,500), carbonic anhydrase (molecular weight: 32,500), soybean trypsin inhibitor (molecular weight: 27,500) and chick egg lysozyme (molecular weight: 18,500).

(7) Isoelectric Point

The isoelectric point was measured by isoelectric focusing, and the catalase of the present invention was found to have an isoelectric point of about 4.8.

The catalase of the present invention is produced by microorganisms, which will be described in detail below.

Examples of such microorganisms include bacteria belonging to the genera Bacillus, Thermus, Micrococcus and the like, yeasts belonging to the genera Hansennula and the like, and fungi belonging to the genera Aspergillus and the like. Among these, a bacterium, especially those belonging to the genus Bacillus, is preferred, and *Bacillus subtilis* is more preferred, with *Bacillus subtilis* IAM 1026 being the most preferred. *Bacillus subtilis* IAM 1026 has been deposited by the inventors with National Institute of Bioscience and Human-Technology, Agency of Industrial Science and Technology under deposit receipt number FERM BP-4844.

*Bacillus subtilis* IAM 1026 is a strain obtained from the Institute of Molecular and Cellular Biology (formerly, the Institute of Applied Microbiology), The University of Tokyo, which is universally available and whose bacteriological properties are well established including its high safety.

In addition to the above, mutants capable of producing the same catalase produced by the above described strain having the aforementioned properties can be obtained using the strain as a parent strain and subjecting it to spontaneous or induced mutation, which can also be used as producer strains of the catalase of the present invention. As an example of conventional means for the preparation of such mutant strains, mutants are derived from the parent strain with no artificial mutagenesis or by subjecting it to artificial mutagenic treatment with ultraviolet rays or a mutagenic drug such as N-methyl-N'-nitro-N-nitrosoguanidine (NTG) or the like, and then a mutant strain of interest is selected from the thus derived mutants making use of its changed property. For example, when a mutant strain having increased catalase productivity is desired, such a selection may be effected by selecting a colony well grown on a medium containing hydrogen peroxide.

The process for producing the catalase of the present invention will be described in detail below.

The aforementioned catalase producing strain is cultured in a usual manner (as described, e.g., in Kumamoto, *J. Sci., Biol.*, vol. 15, no. 2, pp. 39–48 (1981)) under such conditions that it can grow properly. Any medium component may be used provided that it can be utilized by the strain and, as a carbon source for example, glucose, starch syrup, soluble starch or the like may be used preferably. Examples of applicable nitrogen source include ammonium salts, nitrate salts, peptone, meet extract, yeast extract, corn steep liquor, soybean powder and the like. Examples of applicable minerals include phosphates, magnesium salts, potassium salts, calcium salts, cobalt salts, zinc salts, iron salts, borates, molybdenum salts, copper salts and the like. Hydrogen peroxide may be added to the medium, if desired, in an amount of from 20 to 1,000 ppm, preferably from 50 to 200 ppm.

The culturing may be carried out at such a temperature that the producer strain can grow, which is generally from 20° to 40° C. and preferably from 25° to 35° C. The culturing may be carried out at such a pH that the producer strain can grow, which is generally from pH 5 to 9 and preferably from pH 6 to 8.

The catalase of the present invention thus produced can be separated and purified in the following manner.

Any of the generally used enzyme recovering methods can be applied to the recovering of catalase from the culture broth obtained after completion of the culturing. For example, a crude enzyme preparation can be obtained by subjecting the culture broth to centrifugation or filtration to collect cells and then extracting the catalase of interest from the collected cells through the disintegration of te cells making use of a sonicator, a high pressure homogenizer, a French press or a mechanical grinder, the treatment with cyclohexane, toluene, ethyl acetate or the like, or the bacteriolysis with lysozyme.

Purification of the thus obtained crude enzyme preparation may be effected by removing cell debris through a diatomaceous earth filtration or the like means and then carrying out one or a combination of purification procedures optionally selected from conventional enzyme purification techniques, such as ion exchange chromatography, gel filtration, filtration/concentration with an ultrafiltration membrane, ammonium sulfate precipitation, organic solvent precipitation and the like.

While the present invention will be described in more detail below with reference to an example and a comparative example, the present invention is not construed as being limited to the example.

EXAMPLE 1

The catalase according to the present invention was prepared by the following procedures.

After charging a 5 liter capacity jar fermentor with 2 liters of a medium having a composition shown below and sterilizing the medium at 121° C. for 20 minutes, entire portion of *Bacillus subtilis* IAM 1026 cells which have been grown in advance on Scheaffer's agar slant medium contained in 2 test tubes of 24 mm in diameter were inoculated into the jar fermentor medium and cultured for 40 hours under conditions of 7.0 in medium pH, 30° C. in culture temperature, 1 liter/min in aeration rate, and 1,000 rpm in agitation rate. Glucose and ammonia water were added occasionally, and 70 ppm of hydrogen peroxide was added, during the culturing.

| Medium Composition | |
|---|---|
| Glucose | 3.0% |
| Peptone | 0.5% |
| Yeast extract | 0.2% |
| Sodium dihydrogenphosphate dihydrate | 0.57% |
| Dipotassium hydrogenphosphate | 0.61% |
| Ammonium sulfate | 0.3% |
| Magnesium sulfate heptahydrate | 0.3% |
| Inorganic salts of Fe, Mn, Zn, Cu, Co, Mo and B in respective amounts of 0.3 to 20 ppm | |

After completion of the culturing, cells were recovered by centrifugation, suspended in a 50 mM phosphate buffer (pH 7.0) to a concentration of 20% wet cells per total weight, mixed with 300 ppm of lysozyme, and then incubated at 30° C. for 1 hour to effect cell lysis. After filtration treatment using diatomaceous earth, the resulting filtrate was further freed of remaining cells by passing it through a membrane filter for sterile filtration and then concentrated using an ultrafiltration membrane having a nominal molecular weight cutoff of 6,000. As a result, 250 ml of an enzyme solution of 15,000 U/mg protein (120,000 U/ml) was obtained with a purification yield of 86%.

The resulting enzyme was purified by firstly subjecting the enzyme solution to ammonium sulfate precipitation to obtain a fraction at 35 to 50% ammonium sulfate saturation, applying the fraction to a DEAE Cellulofine A-500 column (manufactured by Seikagaku Kogyo Co., Ltd.), and then eluting the enzyme with a gradient of 0 to 0.5M sodium chloride in a 50 mM phosphate buffer. Thereafter, the thus purified preparation was desalted by dialyzing against a 50 mM phosphate buffer using a cellulose tube No. 30 (manufactured by Wako Pure Chemical Industries, Ltd. ).

34 ml of an enzyme solution of 57,000 U/mg protein (740,000 U/ml) was finally obtained.

The quantitative determination of protein was carried out in accordance with the pigment-aided method, as described in the literature (M. Bradford, *Anal. Biochem.*, vol. 72, pp. 248–254 (1976)), using bovine albumin as a standard protein. The catalase activity was measured in accordance with Activity Measuring Method 1 described in the foregoing.

COMPARATIVE EXAMPLE 1

A comparative catalase was prepared by the following procedures.

Catalase producing strain *Bacillus subtilis* 168 was cultured under the same conditions as described in Example 1, and a concentrated catalase solution was prepared from the culture filtrate using an ultrafiltration membrane. 250 ml of the thus obtained catalase solution showed an enzyme concentration of 19,000 U/ml.

Measurement of Optimum Temperature

The enzyme activity was measured in accordance with the aforementioned Activity Measuring Method 2. 1 ml of a diluted sample (5 U/ml) of the enzyme solution obtained in Example 1 was added to 5 ml of the substrate solution which was kept at a temperature of 0°, 10°, 20°, 30°, 40°, 50°, or 60° C., and the reaction was stopped 5 minutes thereafter by adding 2 ml of 1N sulfuric acid. A blank test was carried out by adding 2 ml of 1N sulfuric acid immediately before the addition of the enzyme sample and keeping the mixture for 5 minutes at each reaction temperature. The amount of hydrogen peroxide remained after stopping the reaction was titrated with 0.005N sodium thiosulfate, and relative activity at each temperature was calculated taking the catalase activity at 30° C. as 100. The results are shown in FIG. 2.

As shown in FIG. 2, the catalase of the present invention could exert its function at low temperatures, showing 95% or more (about 100%) of its catalase activity even at 0° C. or 10° C. in comparison with its activity at 30° C.

The catalase of the present invention obtained in Example 1 by ultrafiltration membrane concentration was compared with the catalase of Comparative Example 1 obtained by culturing *Bacillus subtilis* 168 and subjecting the culture filtrate to the same ultrafiltration membrane concentration. The results are shown in Table 1 below.

TABLE 1

(Catalase Activity)

| | Temperature (°C.) | | | | |
|---|---|---|---|---|---|
| | 5 | 10 | 20 | 30 | 40 |
| Example 1 (Catalase of the present invention) | 85 | 87 | 91 | 100 | 84 |
| Comparative Example 1 (Catalase derived from strain 168) | 64 | 66 | 70 | 100 | 86 |

As shown in Table 1, the catalase of the present invention obtained by ultrafiltration membrane concentration had higher catalase activity at low temperatures than that of the comparative catalase obtained by culturing *Bacillus subtilis* 168 and subjecting the culture filtrate to the same ultrafiltration membrane concentration.

Measurement of Thermal Stability

A diluted sample (200 U/ml) of the enzyme solution obtained in Example 1 was incubated for 30 minutes at pH 7.0 under each of varied temperature conditions (20°, 30°, 40°, 50°, and 60° C.), and the residual activity was measured in accordance with the aforementioned Activity Measuring Method 2. The results are shown in FIG. 3 as relative values calculated by taking the residual activity at 30° C. as 100. The enzyme of the present invention was stable at up to 50° C., but its residual activity at 60° C. was found to be 34%.

Measurement of Optimum pH

The enzyme activity was measured in accordance with the aforementioned Activity Measuring Method 2. 1 ml of a diluted sample (5 U/ml) of the enzyme solution obtained in Example 1 was added to 5 ml of a substrate solution kept at 30° C., which has been prepared using a buffer solution having a pH value of 4, 5, 6, 7, 8, 9, 10, 11, 11.5, or 12, and the reaction was stopped 5 minutes thereafter by adding 2 ml of 1N sulfuric acid. A blank test was carried out by adding 2 ml of 1N sulfuric acid immediately before the addition of the enzyme sample and keeping the mixture for 5 minutes at 30° C. The amount of hydrogen peroxide remained after stopping the reaction was titrated with 0.005N sodium thiosulfate, and relative activity at each pH was calculated taking the catalase activity at pH 7.0 as 100. The results are shown in FIG. 4.

As shown in FIG. 4, the catalase of the present invention has an optimum pH range of from 7 to 10 and shows 95% or more of its activity at pH 7 within the pH range of from 7 to 10. The buffer solutions used are a 50 mM acetate buffer for pH 4 to 5, a 50 mM phosphate buffer for pH 5 to 9, and a 50 mM glycine buffer for pH 9 to 12.

Measurement of pH stability

A diluted sample (200 U/ml) of the enzyme solution obtained in Example 1 was incubated for 30 minutes at 30° C. under each of varied pH conditions (4, 5, 6, 7, 8, 9, 10, 11, 11.5, and 12), and the residual activity was measured in accordance with the aforementioned Activity Measuring Method 2. The results are shown in FIG. 5 as relative values calculated by taking the residual activity at pH 7 as 100. The enzyme of the present invention was stable at pH 6 to 10.

Measurement of Fluoride Ion Resistance

The enzyme activity was measured in accordance with the aforementioned Activity Measuring Method 1. 100 μl of a diluted sample (40 U/ml) of the enzyme solution obtained in Example 1 was added to 3 ml of a hydrogen peroxide substrate solution containing 10 mM potassium fluoride, which has been prepared using a 50 mM phosphate buffer, and decrease in the absorbance at 240 nm per 1 minute was measured to compare the results with the case of the absence of potassium fluoride.

The catalase of the present invention had resistance to 10 mM potassium fluoride, since it showed 96% of its activity even in the presence of 10 mM potassium fluoride in comparison with the case of the absence of the compound.

Measurement of Isoelectric Point

An isoelectric point of the catalase of the present invention was measured using the enzyme solution obtained in Example 1 (740,000 U/ml) as a sample and making use of Phast system (manufactured by Pharmacia Corp.). The measurement was carried out using a gradient gel of pH 4 to 6.5, with about 1 unit of the enzyme and at a temperature of 24° C.

Catalase in the gel was detected by an active staining method, as described in the literature (D. A. Clare, *Analytical Biochemistry*, vol. 140, p. 532–537 (1984)). A gel was soaked for 45 minutes in a 50 mM phosphate buffer (pH 7) containing 50 μg/ml of horseradish peroxidase, soaked for another 10 minutes after adding hydrogen peroxide to a final concentration of 5 mM, washed twice with water, and then soaked in a 50 mM phosphate buffer (pH 7.0) containing 0.5 mg/ml of diaminobenzidine to carry out the reaction until formation of a catalase-specific band. Thereafter, the gel was soaked in 5% glycerol solution and then air-dried.

Isoelectric point markers were subjected to Coomassie staining. As a result, the isoelectric point of the catalase of the present invention was found to be about 4.8.

Since the catalase of the present invention shows high catalase activity even at low temperatures, it is useful in a process for the removal of hydrogen peroxide that is desirably carried out at a low temperature. Also, since a temperature-increasing step for attaining efficient enzyme reaction can be eliminated, it is especially effective for water treatment in the winter season or in cold districts. Since it can function even in alkaline range and has fluoride ion resistance, it is effective for the treatment of hydrogen peroxide-containing waste water for example in semiconductor industries and can be used for the hydrolysis of hydrogen peroxide remained after bleaching of fiber or herring roe.

Furthermore, the catalase of the present invention can be obtained efficiently by culturing *Bacillus subtilis* IAM 1026 and recovering the enzyme from the cultured cells.

While the invention has been described in detail and with reference to specific examples thereof, it will be apparent to one skilled in the art that various changes and modifications can be made therein without departing from the spirit and scope thereof.

What is claimed is:

1. An isolated catalase obtained from a microorganism of the genus Bacillus having a catalase activity at 0° C. of 95% or more of its catalase activity at 30° C., when measured at pH 7 and wherein said catalase has:

(1) an operative temperature of 0° to 60° C. and an optimum temperature of 0° to 30° C., when measured within the range of from 0° to 60° C., (2) an optimum pH of 7 to 10, (3) a resistance to 10 mM potassium fluoride, (4) a molecular weight of 65,000±3,000, when measured by SDS polyacrylamide gel electrophoresis, and (5) an isoelectric point of about 4.8, when measured by isoelectric focusing.

2. An isolated catalase obtained from *Bacillus subtilis* having a catalase activity at 0° C. of 95% or more of its catalase activity at 30° C., when measured at pH 7 and wherein said catalase has:

(1) an operative temperature of 0° to 60° C. and an optimum temperature of 0° to 30° C., when measured within the range of from 0° to 60° C., (2) an optimum pH of 7 to 10, (3) a resistance to 10 mM potassium fluoride, (4) a molecular weight of 65,000±3,000, when measured by SDS polyacrylamide gel electrophoresis, and (5) an isoelectric point of about 4.8, when measured by isoelectric focusing.

3. A process for producing a catalase comprising culturing a microorganism of the genus Bacillus to obtain said catalase, said catalase having a catalase activity at 0° C. of 95% or more of its catalase activity at 30° C., when measured at pH 7 and wherein said catalase has:

(1) an operative temperature of 0° to 60° C. and an optimum temperature of 0° to 30° C., when measured within the range of from 0° to 60° C., (2) an optimum pH of 7 to 10, (3) a resistance to 10 mM potassium fluoride, (4) a molecular weight of 65,000±3,000, when measured by SDS polyacrylamide gel electrophoresis, and (5) an isoelectric point of about 4.8, when measured by isoelectric focusing.

4. A process for producing a catalase comprising culturing *Bacillus subtilis* to produce said catalase, said catalase having a catalase activity at 0° C. of 95% or more of its catalase activity at 30° C., when measured at pH 7 and wherein said catalase has:

(1) an operative temperature of 0° to 60° C. and an optimum temperature of 0° to 30° C., when measured within the range of from 0° to 60° C., (2) an optimum pH of 7 to 10, (3) a resistance to 10 mM potassium fluoride, (4) a molecular weight of 65,000±3,000, when measured by SDS polyacrylamide gel electrophoresis, and (5) an isoelectric point of about 4.8, when measured by isoelectric focusing.

* * * * *